United States Patent [19]

Brown et al.

[11] Patent Number: 5,051,508
[45] Date of Patent: Sep. 24, 1991

[54] DIHYDROPYRROLO QUINOLINE DERIVATIVES

[75] Inventors: Thomas H. Brown, Tewin; Robert J. Ife; Colin A. Leach, both of Stevenage, all of England

[73] Assignee: SmithKline Beckman Intercredit B.V., Rotterdam, Netherlands

[21] Appl. No.: 540,394

[22] Filed: Jun. 19, 1990

Related U.S. Application Data

[63] Continuation of Ser. No. 218,757, Jul. 13, 1988, abandoned.

[30] Foreign Application Priority Data

Jul. 24, 1987 [GB] United Kingdom ............... 8717644

[51] Int. Cl.$^5$ ............................................ C07D 471/04
[52] U.S. Cl. ......................................... 546/84; 546/88
[58] Field of Search ................................ 546/84, 88

[56] References Cited

U.S. PATENT DOCUMENTS 2,691,023 10/1954 Hörlein et al. ...................... 546/84

FOREIGN PATENT DOCUMENTS 2258855 8/1975 France .
725745 3/1955 United Kingdom .

OTHER PUBLICATIONS

T. Ozawa et al., *J. Pharm. Soc. Japan*, 77, 85-89 (1957) (*Chem. Abstracts* 51, 8749h, (1957)).
Nagaoka, S., *J. Pharm. Soc. Japan*, 81, 363-369 (1961) (*Chem. Abstracts*, 55, 154906 (1961)(.
Nagaoka, S., *J. Pharm. Soc. Japan*, 81, 479-483 (1961) (*Chem. Abstracts*, 55, 19922g (1961)).
M. Grundon et al., *J. Chem. Soc.*, pp. 3448-3450 (1957).
B. McDonald et al., *J.C.S. Perkin I*, pp. 1446-1450 (1985).
*Chem. Abstracts* 49: 14813c (1955).
Ozawa, T. et al., *J. Pharm. Soc. Japan*, 77, 90-93 (1961).
*Chemical Abstracts*, 84: 4825e (1976).

*Primary Examiner*—Mary C. Lee
*Assistant Examiner*—Joseph K. McKane
*Attorney, Agent, or Firm*—Charles M. Kinzig; Stuart R. Suter; Edward T. Lentz

[57] ABSTRACT 1,4-Substituted 2,3-dihydropyrrolo[3,2-c]quinolines which are inhibitors of H+K+ATPase activity and useful as inhibitors of gastric acid secretion. A compound of the invention is 1-(2-methylphenyl)-4-amino-6-methyl-2,3-dihydropyrrolo[3,2-c]quinoline.

21 Claims, No Drawings

DIHYDROPYRROLO QUINOLINE DERIVATIVES

This is a continuation of application Ser. No. 07/218,757, filed July 13, 1988, now abandoned.

The present invention relates to substituted quinoline derivatives, processes for their preparation, intermediates useful in their preparation, pharmaceutical compositions containing them and their use in therapy.

Substituted quinoline derivatives are known in the art. For example, in J.Chem.Soc. 1957, 3448, J.Pharm.Soc.Japan 1961, 18, 363, 1961 and 479, certain 1-(substituted phenyl)-4-methyl-2,3-dihydropyrrolo[3,2-c]quinolines, 1-phenyl-4-halo-2,3-dihydropyrrolo[3,2-c]quinolines and 1-phenyl-2,3-dihydropyrrolo[3,2-c]quinolines are disclosed as synthetic intermediates but no therapeutic activity is disclosed for such compounds. In addition. J.Pharm.Soc.Japan 1957, 77, 85, and ibid. 1961, 90, disclose certain 1-(substituted phenyl)-4-methyl-2,3-dihydropyrrolo[3,2-c]quinolines and report antibacterial activity for the compounds but do not disclose formulations containing said compounds or information concerning a specific therapeutic utility for the compounds. It has now been found that certain substituted 2,3-dihydropyrrolo[3,2-c]quinolines are potent inhibitors of the H+K+ATpase enzyme and as such are useful as antiulcer agents.

Accordingly the present invention provides, in a first aspect compounds of structure (I)

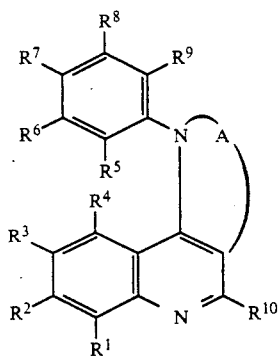

(I)

in which $R^1$ to $R^4$ are the same or different and are each hydrogen, $C_{1-4}$alkyl, $C_{1-6}$alkoxy, phenyl, $C_{1-6}$alkylthio, $C_{1-4}$alkanoyl, amino, $C_{1-6}$alkylamino, di$C_{1-6}$alkylamino, halogen, trifluoromethyl or nitro, provided that at least two of $R^1$ to $R^4$ are hydrogen.

$R^5$ to $R^9$ are the same or different and are each hydrogen, $C_{1-6}$alkyl, $C_{1-6}$alkoxy, $C_{1-6}$alkylthio, halogen, cyano, amino, hydroxy, carbamoyl, carboxy, $C_{1-6}$alkanoyl, trifluoromethyl or nitro, provided that at least two of $R^5$ to $R^9$ are hydrogen;

$R^{10}$ is hydrogen, $C_{1-6}$alkyl, $C_{1-6}$alkoxy, halogen, hydroxy, —$CH_2OH$, $C_{1-6}$alkylthio, $NH(CH_2)_nOH$ in which n is 0 to 4 or a group —$NR^{11}R^{12}$ in which $R^{11}$ and $R^{12}$ are the same or different and are each hydrogen or $C_{1-6}$alkyl; and A is —$(CH_2)_2$—, —$(CH_2)_3$— or —CH=CH—; provided that (i) when $R^1$ to $R^7$ are each hydrogen, one of $R^8$ and $R^9$ is hydrogen and the other is hydrogen or methoxy and $R^{10}$ is methyl, A is —$(CH_2)_3$— or —CH=CH—;

(ii) when $R^1$ to $R^6$ and $R^8$ and $R^9$ are each hydrogen, $R^7$ is hydroxy and is methyl, A is $(CH_2)_3$— or —CH=CH—;

(iii) when $R^1$ to $R^9$ are each hydrogen and is chlorine, A is —$(CH_2)_3$—;

(iv) when $R^1$ to $R^{10}$ are each hydrogen. A is —$(CH_2)_3$—;

(v) when $R^1$ and $R^2$ and $R^4$ to are each hydrogen and $R^3$ is methoxy, A is —$(CH_2)_2$— or —$(CH_2)_3$—;

(vi) when $R^2$ to $R^9$ are each hydrogen, $R^{10}$ is methyl and $R^1$ is hydrogen, hydroxy or methoxy, A is —$(CH_2)_3$— or —CH=CH—;

(vii) when $R^1$ to $R^6$ and $R^8$ and $R^9$ are each hydrogen, $R^{10}$ is methyl and $R^7$ is methyl or methoxy, A is —$(CH_2)_3$— is or —CH TM CH—;

(viii) when $R^1$ to $R^8$ are each hydrogen, $R^9$ is chlorine and is methyl, A is —$(CH_2)_3$ or —CH=CH—, and pharmaceutically acceptable salts thereof.

Suitably A is —$(CH_2)_3$—, preferably A is —$(CH_2)_2$— or —CH=CH—.

Suitably, $R^1$ to $R^4$ are all hydrogen; more suitably only two of $R^1$ to $R^4$ are hydrogen, preferably three of $R^1$ to $R^4$ are hydrogen. More preferably $R^2$ to $R^4$ are hydrogen and $R^1$ is other than hydrogen. Most preferably $R^2$ to $R^4$ are hydrogen and $R^1$ is $C_{1-6}$alkyl or $C_{1-6}$alkoxy.

Suitably $R^5$ to $R^9$ are all hydrogen. Preferably three or $R^5$ to $R^9$ are hydrogen. More preferably $R^5$ to $R^8$ are all hydrogen and $R^9$ is other than hydrogen. Most preferably $R^5$ to $R^8$ are all hydrogen and $R^9$ is $C_{1-6}$alkyl, in particular, methyl.

Suitably $R^{10}$ is halogen or $C_{1-6}$alkylthio. Preferably $R^{10}$ is hydrogen, or a group $NR^{11}R^{12}$.

Preferably $R^{11}$ and $R^{12}$ are the same or different and are each hydrogen or $C_{1-6}$alkyl.

$C_{1-6}$alkyl groups (either alone or as part of another group) can be straight or branched.

It will be appreciated that compounds of structure (I) in which one or more of $R^1$ to $R^{10}$ is a $C_{3-6}$alkyl group (either alone or as part of another group) may contain an assymetric centre due to the presence of the $C_{3-6}$alkyl group. Such compounds will exist as two (or more) optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides in a further aspect a process for the preparation of a compound of structure (I) or a pharmaceutically acceptable salt thereof which comprises (a) for compounds in which $R^{10}$ is hydrogen or $C_{1-6}$alkyl. cyclisation of a compound of structure

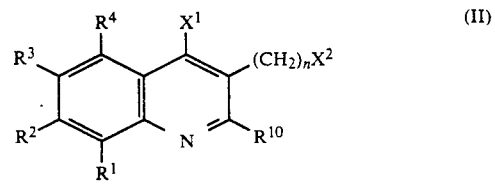

(II)

in which $R^1$ to $R^4$ are as described for structure (I), and $R^{10}$ is as described for structure (I) or a leaving group, n is 2 or 3 and $X^1$ and $X^2$ are leaving groups, in the presence of a compound of structure (III)

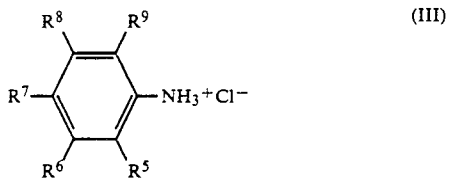

in which $R^5$ to $R^9$ are as described for structure (I); or (b) for compounds in which $R^{10}$ is other than $C_{1-6}$alkyl reaction of a compound of structure (IV)

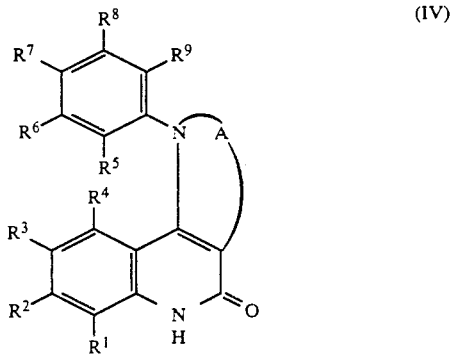

in which $R^1$ to $R^9$ and A are as described for structure (I) with a reagent providing the group $R^{10}$, and optionally therafter
converting one group $R^{10}$ into another group $R^{10}$;
oxidising a compound in which A is $(CH_2)_2$ to a compound in which A is $-CH=CH-$;
removing any protecting groups;
forming a pharmaceutically acceptable salt.

Suitable leaving groups $X^1$ and $X^2$ will be apparent to those skilled in the art and include for example halogen, in particular chlorine. Suitable leaving groups for $R^{10}$ will also be apparent to those skilled in the art and include for example $C_{1-4}$alkylsulphinyl, particularly methylsulphinyl.

Suitably the cyclisation of a compound of structure (II) in the presence of a compound of structure (III) is carried out in a solvent and at a temperature of between ambient and the reflux temperature of the solvent used. Preferably the reaction is carried out at elevated temperature under pressure in a suitable solvent. For example, in a solvent such as 2-propanol at a temperature of 160°–180° at a pressure of between 50–150 p.s.i.

Suitable reagents providing the group $R^{10}$ will be apparent to those skilled in the art and will of course depend on the nature of the group $R^{10}$ sought. For example in the preparation of compounds of structure (I) in which $R^{10}$ is halogen, or example chlorine, a suitable compound of structure (Iv) can be reacted with phosphorous oxychloride, optionally in the presence of a suitable solvent and at an appropriate temperature; for compounds of structure (I) in which $R^{10}$ is $NH_2$, a suitable compound of structure (Iv) can be reacted with phenyl phosphorodiamidate, again optionally in the presence of a suitable solvent at an appropriate temperature.

Alternatively, compounds of structure (I) can be prepared from other compounds of structure (I), or example, compounds of structure (I) in which $R^{10}$ is halogen can be converted into compounds of structure (I) in which $R^{10}$ is other than halogen by reaction with an appropriate nucleophilic reagent capable of displacing the chlorine atom. Suitable nucleophilic reagents include for example an amine such as a $C_{1-4}$alkylamine, for example methylamine in a suitable solvent such as methanol; such reagents can be used to form compounds of structure (I) in which $R^{10}$ is $C_{1-4}$alkylamino, particularly, methylamino. In addition compounds of structure (I) in which $R^{10}$ is methyl can be converted into compounds of structure (I) in which $R^{10}$ is $CH_2OH$, in two steps, firstly by oxidation of the adjacent ring nitrogen atom with, or example, m-chloroperbenzoic acid followed by rearrangement in the presence of, for example, trifluoroacetic anhydride.

Further interconversions will be apparent to those skilled in the art, for example, compounds of structure (I) in which A is $-(CH_2)_3-$ and $R^{10}$ is hydrogen, can be converted to compounds of structure (Iv) in which A is $-(CH_2)_3-$, in two steps, firstly by oxidation of the quinoline nitrogen atom, with for example, m-chloroperbenzoic acid followed by rearrangement in the presence of for example, trifluoroacetic anhydride.

Suitable reagents for carrying out the oxidation of compounds of structure (I) in which A is $(CH_2)_2$ to compounds of structure (I) in which A is $CH=CH$ will be apparent to those skilled in the art and include, for example, dehydrogenation in the presence of a noble metal catalyst, in particular palladium-on-carbon.

Pharmaceutically acceptable acid addition salts of the compounds of structure (I) can be prepared by standard procedures by, for example, reaction with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as, for example, citric, maleic or fumaric acids.

Certain intermediate compounds of structure (II) and (IV) are new and as such form a further aspect of the present invention. They can be prepared by procedures analogous to those known in the art. For example, compounds of structure (II) can be prepared by heating a compound of structure (V) and a compound of structure (VI)

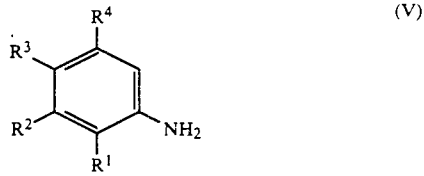

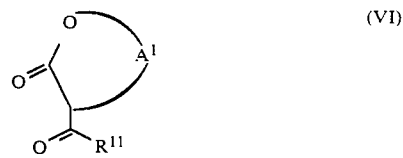

in which, $R^1$ to $R^4$ are as described for structure (I), $R^{11}$ is hydrogen or $C_{1-4}$alkyl and A is $(CH_2)_2-$ or $-(CH_2)_3-$ optionally in the presence of a suitable solvent, followed by treatment with, for example, phosphorous oxychloride.

Compounds of structure (IV) in which $R^1$ to $R^4$ are the same as $R^6$ to $R^9$ and $R^5$ is hydrogen can be prepared by the reactions outlined in Scheme (I) below.

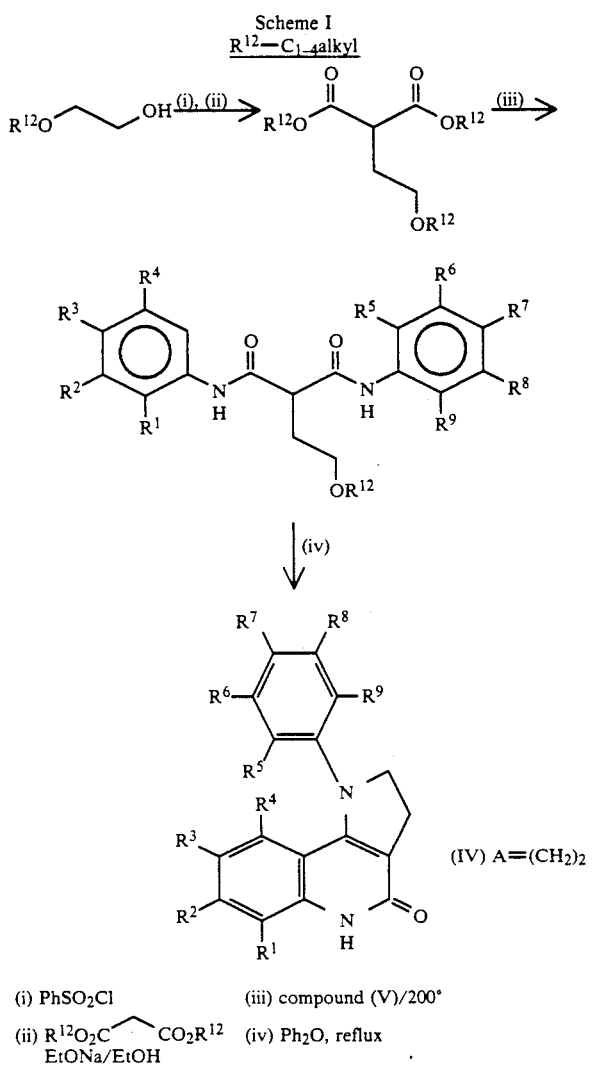

(i) PhSO$_2$Cl  (iii) compound (V)/200°
(ii) R$^{12}$O$_2$C⌢CO$_2$R$^{12}$  (iv) Ph$_2$O, reflux
    EtONa/EtOH The compounds of structure (IV) so formed can be converted into the corresponding compounds of structure (IV) in which A is CH=CH by oxidation in the presence of a palladium/carbon catalyst.

It is to be noted, and apparent to those skilled in the art that in the foregoing reactions, where necessary, groups $R^1$ to $R^9$ will be in protected form when undergoing the procedures described.

For example, in carrying out the reaction step (iv) of Scheme 1 any hydroxy or amino groups present in said substituents should be protected. Suitable protecting groups are as described in "Greene, T. W., protective Groups in Organic Chemistry".

The compounds of structure (I) and their pharmaceutically acceptable salts and related compounds for which no pharmaceutical utility has been previously disclosed exert an anti-secretory effect by inhibition of the gastrointestinal H+K+ATpase enzyme (Fellenius E., Berglindh T., Sachs G., Olke L., Elander B., Sjostrand S. E., and Wahlmark B., 1981, Nature, 290, 159–61).

In a further aspect therefore the present invention provides the use of the compounds of structure (IA)

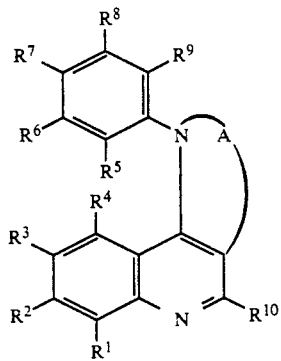

in which
$R^1$ to $R^4$ are the same or different and are each hydrogen, $C_{1-4}$alkyl, $C_{1-6}$alkoxy, phenyl. $C_{1-6}$alkylthio, $C_{1-6}$alkanoyl, amino, $C_{1-6}$alkylamino, di$C_{1-6}$alkylamino, halogen, trifluoromethyl or nitro, provided that at least two of $R^1$ to $R^4$ are hydrogen.

$R^5$ to $R^9$ same or different and are each hydrogen, $C_{1-6}$alkyl, $C_{1-6}$alkoxy, $C_{1-6}$alkylthio, halogen, cyano, amino, hydroxy, carbamoyl, carboxy, $C_{1-6}$alkanoyl, trifluoromethyl or nitro, provided that at least two of $R^5$ to $R^9$ are hydrogen;

$R^{10}$ is hydrogen, $C_{1-6}$alkyl, $C_{1-6}$alkoxy, halogen, hydroxy, —CH$_2$OH, $C_{1-6}$alkylthio, NH(CH$_2$)$_n$OH in which n is 0 to 4 or a group —NR$^{11}$R$^{12}$ in which $R^{11}$ and $R^{12}$ are the same or different and are each hydrogen or $C_{1-6}$alkyl; and A is —(CH$_2$)$_2$—, —(CH$_2$)$_3$— or —CH=CH—; provided that (i) when $R^2$ to $R^9$ are each hydrogen, $R^{10}$ is methyl and $R^1$ is hydrogen, hydroxy or methoxy, A is —(CH$_2$)$_3$— or —CH=CH—;

(ii) $R^1$ to $R^6$ and $R^8$ and $R^9$ are each hydrogen, $R^{10}$ is methyl and $R^7$ is methyl or methoxy, A is —(CH$_2$)$_3$— or —CH=CH—;

(iii) when $R^1$ to $R^8$ are each hydrogen, $R^9$ is chlorine and $R^{10}$ is methyl, A is —(CH$_2$)$_3$ or —CH=CH—, and pharmaceutically acceptable salts thereof in therapy. The compounds of structure (IA) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, and Zollinger-Ellison Syndrome In a still further aspect there is therefore provided compounds of structure (IB)

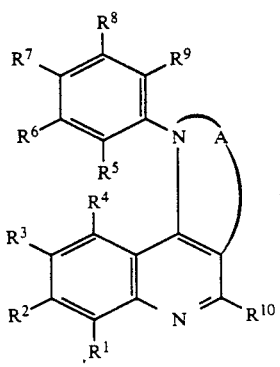

in which $R^1$ to $R^4$ are the same or different and are each hydrogen, $C_{1-4}$alkyl, $C_{1-6}$alkoxy, phenyl, $C_{1-6}$alkylthio, $C_{1-6}$alkanoyl, amino, $C_{1-6}$alkylamino, di$C_{1-6}$alkylamino, halogen, trifluoromethyl or nitro, provided that at least two of $R^1$ to $R^4$ are hydrogen.

$R^5$ to $R^9$ are the same or different and are each hydrogen, $C_{1-6}$alkoxy, $C_{1-6}$alkoxy, $C_{1-6}$alkylthio, halogen, cyano, amino, hydroxy, carbamoyl, carboxy. $C_{1-6}$alkanoyl, trifluoromethyl or nitro, provided that at least two of $R^5$ to $R^9$ are hydrogen;

$R^{10}$ is hydrogen, $C_{1-6}$alkyl, $C_{1-6}$alkoxy, halogen, hydroxy, —$CH_2OH$, $C_{1-6}$alkylthio, $NH(CH_2)_nOH$ in which n is 0 to 4 or a group —$NR^{11}R^{12}$ in which $R^{11}$ and $R^{12}$ are the same or different and are each hydrogen or $C_{1-6}$alkyl; and A is —$(CH_2)_2$—, —$(CH_2)_3$— or —$CH=CH$—;

or a pharmaceutically acceptable salt thereof for use in the preparation of a medicament for use in the treatment of ulcer disease.

Further, the compounds of structure (IB) can be used in the treatment of other disorders where an anti-secretory effect is desirable for example in patients with gastritis, NSAID induced gastritis, gastric ulcers, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (IB) or a pharmaceutically acceptable salt thereof and a pharmaceutically acceptable carrier.

The compounds of structure (IB) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (IB) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of structure (IB) or a pharmaceutically acceptable salt thereof calculated as the free base.

The present invention also provides a method of inhibiting gastric acid secretion which comprises administering to a mammal in need thereof an effective amount of a compound of structure (IB) or a pharmaceutically acceptable salt thereof; and a method of treatment of diseases of the stomach or intestine based on increased acid secretion which comprises administering to a mammal in need thereof an effective amount of a compound of structure (IB) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of structure (IB) or a pharmaceutically acceptable salt thereof calculated as the free base, the compound being administered 1 to 4 times per day. Suitably the compounds will be administered for a period of continuous therapy, or example for a week or more.

In addition, the compounds of the present invention can be co-administered with further active ingredients, such as antacids (for example magnesium carbonate or hydroxide and aluminium hydroxide). non-steroidal antiflammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$-antagonists (for example, cimetidine).

The following examples illustrate the invention. Temperatures are recorded in degrees centigrade.

EXAMPLE 1

Preparation of
1-(2-methoxyphenyl)-4-methyl-6-methoxy-2,3-dihydropyrrolo[3,2-c]quinoline 2-Methyl-3-(2-chloroethyl)-4-chloro-8-methoxyquinoline (2.70 g, 10 mmol) and 2-methoxyaniline hydrochloride (1.60 g, 10 mmol) in 1-butanol (40 ml) were heated at reflux for 6 hours then the solvent evaporated, the crude product taken up in dichloromethane, washed with aqueous sodium bicarbonate, dried and evaporated. Trituration with ether and recrystallisation from aqueous methanol gave 1-(2-methoxyphenyl)-4-methyl-6-methoxy-2,3-dihydropyrrolo[3,2-c]quinoline (0.62 g, 19%), m.p. 168°–169°.

$C_{20}H_{20}N_2O_2$: Found: C 74.84, H 6.33, N 8.53. Requires: C 74.98, H 6.29, N 8.74.

EXAMPLE 2

Preparation of 1-(2-methylphenyl)-4-methyl-6-methoxy-2,3-dihydropyrrolo[3,2-c]quinoline 2-Methyl-3-(2-chloroethyl)-4-chloro-8-methoxyquinoline (8.37 g, 31 mmol) and 2-methylaniline hydrochloride (4.45 g, 31 mmol) in 1-butanol (100 ml) were heated at reflux for 5 days, then the solvent evaporated, the crude product taken up in dichloromethane, washed with aqueous sodium bicarbonate, dried and evaporated. Chromatography (silica gel, 2% methanolic ammonia in dichloromethane) and recrystallisation from aqueous ethanol gave 1-(2-methylphenyl)-4-methyl-6-methoxy-2,3-dihydropyrrolo[3,2-c]quinoline (2.04 g, 22 %), m.p. 182°–183°.

$C_{20}H_{20}N_2O$: Found: C 79.04, H 6.50, N 9.21. Requires: C 78.92, H 6.62, N 9.20.

EXAMPLE 3

Preparation of 1-(2-methylphenyl)-4-methyl-6-hydroxy-2,3-dihydropyrrolo[3,2-c]quinoline 2-Methyl-3-(2-chloroethyl)-4-chloro-8-methoxyquinoline (54 g, 0.2 mol), o-methylaniline hydrochloride (28.7 g, 0.2 mol) and 1-butanol (500 ml) were heated to 17° C. in a pressure vessel for 10 hours, then the solvent evaporated. Conversion to free base and chromatography (silica gel, 2% methanolic ammonia in dichloromethane) gave 1-(2-methylphenyl)-4-methyl-6-methoxy-2,3-dihydropyrrolo[3,2-c]quinoline in the early fractions. Later fractions were recrystallised from ethyl acetate to yield 1-(2-methylphenyl)-4-methyl-6-hydroxy-2,3-dihydropyrrolo[3,2-c]quinoline, m.p. 144°–146°.

$C_{19}H_{18}N_2O$: Found: C 78.49, H 6.39, N 9.70. Requires: C 78.59, H 6.25, N 9.65.

EXAMPLE 4

Preparation of 1-(2-methylphenyl)-4-methyl-6-methoxypyrrolo[3,2-c]quinoline 1-(2-Methylphenyl)-4-methyl-6-methoxy-2,3-dihydropyrrolo[3,2-c]quinoline (4.57 g, 15 mmol) in diphenyl ether (50 ml) was heated at reflux with 10% palladium-on-charcoal (1.0 g) for 1 hour then the catalyst removed on celite. Chromatography (silica gel, 1% methanolic ammonia in dichloromethane) and recrystallisation from ethyl acetate/petroleum ether gave 1-(2-methylphenyl)-4-methyl-6methoxypyrrolo[3,2-c]quinoline(2.2 g, 48%), m.p. 143°–145°.

$C_{20}H_{18}N_2O$: Found: C 79.22, H 6.05, N 9.23. Requires: C 79.44, H 6.00, N 9.26.

EXAMPLE 5

Preparation of 1-(2-methylphenyl)-4,6-dimethyl-2,3-dihydropyrrolo[3,2-c]quinoline 2,8-Dimethyl-3-(2-chloroethyl)-4-chloroquinoline (7.63 g, 30 mmol) and 2-methylaniline hydrochloride (4.31 g, 30 mmol) in 1-butanol (100 ml) were heated at reflux for 4 days, then the solvent evaporated, the crude product taken up in dichloromethane, washed with aqueous sodium bicarbonate, dried and evaporated. Chromatography (silica gel, 2% methanolic ammonia in dichloromethane) and recrystallisation from aqueous ethanol gave 1-(2-methylphenyl)-4,6-dimethyl-2,3-dihydropyrrolo-[3,2-c]quinoline (1.95 g, 23%), m.p. 126°–128°.

$C_{20}H_{20}N_2$: Found: C 83.11, H 7.06, N 9.65. Requires: C 83.30, H 6.99, N 9.71.

EXAMPLE 6

Preparation of 1-(2-methylphenyl)-4-methyl-2,3-dihydropyrrolo[3,2-c]quinoline

2-Methyl-3-(2-chloroethyl)-4-chloroquinoline (45 g, 0.16 mol), 2-methylaniline (35 ml, 0.32 mol) and ethanol (300 ml) were heated to 150° C. in a pressure vessel for 17 hours, then concentrated in vacuo. The product crystallised as the hydrochloride salt. Conversion to free base and recrystallisation from ethyl acetate yielded 1-(2-methylphenyl)-4-methyl-2,3-dihydropyrrolo[3,2-c]quinoline (19.1 g, 43%), m.p. 148°–150°.

$C_{19}H_{18}N_2$:
Found: C 83,25, H 6.66, N 10.20.
Requires: C 83.18, H 6.61, N 10.21.

EXAMPLE 7

Preparation of 1-(4-methoxy-2-methylphenyl)-4-methyl-2,3-dihydropyrrolo3,2-c]quinoline 2-Methyl-3-(2-chloroethyl)-4-chloroquinoline hydrochloride (5.53 g, 20 mmol) and 4-methoxy-2-methylaniline (5.15 ml, 40 mmol) in ethanol (100 ml) were heated at 170° C. in a pressure vessel for 24 hours, then the solvent evaporated, the crude product taken up in dichloromethane, washed with aqueous sodium bicarbonate, dried and evaporated. Chromatography (silica gel, 2% methanolic ammonia in dichloromethane) and recrystallisation from aqueous methanol gave 1-(4-methoxy-2-methylphenyl)-4-methyl-2,3-dihydropyrrolo[3,2-c]quinoline (2.04 g, 22 %), m.p. 115°–117°.

$C_{20}H_{20}N_2O$. $0.4H_2O$.
Found: C 77.07, H 6.70, N 8.85.
Requires: C 77.09, H 6.73, N 8.99.

EXAMPLE 8

Preparation of 1-(2-methylphenyl)-7-methoxy-1,2,3,4-tetrahydropyridino[3,2-c]quinoline A. Preparation of 3-(2-methoxyphenylaminomethylene)tetrahydropyran-2-one The sodium salt of 3-(hydroxymethylene)-tetrahydropyran-2-one (25 g, 0.17 mol) and 2-methoxyaniline hydrochloride (32 g, 0.2 mol) in ethanol (750 ml) were warmed to 70° C. with stirring for 2 hours, then filtered hot. After evaporation of the ethanol, the crude product was taken up in dichloromethane, washed with dilute hydrochloric acid, dried and evaporated. Trituration with ether gave 3-(2-methoxyphenylaminomethylene)-tetrahydropyran-2-one (21.5 g, 55%) as a mixture of E and Z isomers, m.p. 85°–100°.

B. preparation of 3-(3-chloropropyl)-4-chloro-8-methoxyquinoline 3-(2-Methoxyphenylaminomethylene)-tetrahydropyran-2-one (11.67 g. 50 mmol) in phosphoryl chloride (50 ml) was heated at reflux for 1 hour. After cooling, the solution was poured onto ice, the mixture heated to boiling, charcoal added, and the hot solution filtered through celite. Subsequent cooling and addition of sodium hydroxide solution gave a solid which was filtered off and recrystallised from aqueous ethanol to yield 3-(3-chloropropyl)-4-chloro-8-methoxyquinoline (5.6 g, 41%), m.p. 86°–89°.

C. preparation of 1-(2-methylphenyl)-7-methoxy-1,2,3,4-tetrahydropyridino[3,2-c]quinoline A solution of 3-(3-chloropropyl)-4-chloro-8-methoxyquinoline (6.4 g, 23.6 mmol) and 2-methylaniline (5.0 ml, 47.2 mmol) in ethanol (250 ml) was heated at reflux for 4 days, then cooled and evaporated. Dichloromethane and aqueous sodium bicarbonate solution were added, and the organic layer washed with water, dried and evaporated. Chromatography (silica gel, 1% methanolic ammonia in dichloromethane) followed by crystallisation from ethyl acetate gave 1-(2-methylphenyl)-7-methoxy-1,2,3,4-tetrahydropyridino-[3,2-c]quinoline (1.92 g, 27%), m.p. 160°–161°.

$C_{20}H_{20}N_2O$: Found: C 78.80, H 6.57, N 9.23. Required: C 78.92, H 6.62, N 9.20.

EXAMPLE 9

Preparation of 1-(2-methoxyphenyl)-4-oxo-6-methoxy-2,3,4,5-tetrahydropyrrolo[3,2-c]quinoline A. Preparation of 2-(2-ethoxyethyl)-N,N'-di(2-methoxyphenyl)malonodiamide A mixture of o-anisidine (45.1 ml, 0.4 mol) and diethyl 2-ethoxyethylmalonate (46.5 g, 0.2 mol) was heated to 200° C. as nitrogen was bubbled slowly through the mixture, and ethanol allowed to distill off. After 3 hours the crude product was allowed to cool and triturated with petroleum ether. The solid was filtered off and recrystallised from ethyl acetate/petroleum ether to give 2-(2-ethoxyethyl)-N,N'-di(2-methoxyphenyl)-malonodiamide (36.6 g, 47%), m.p. 132°–133°.

B. Preparation of 1-(2-methoxyphenyl)-4-oxo-6-methoxy-2,3,4,5-tetrahydropyrrolo[3,2-c]quinoline 2-(2-Ethoxyethyl)-N,N'-di(2-methoxyphenyl)-malonodiamide (31 g, 80 mmol) was stirred for 9 hours in diphenyl ether (120 ml) at reflux. The mixture was allowed to cool, diluted with petroleum ether, and the resulting solid filtered off. This was a mixture of the desired product plus 4-oxo-6-methoxy-2,3,4,5-tetrahydrofuro[3,2-c]quinoline. Repeated chromatography (silica gel, 1.5% methanolic ammonia in dichloromethane) followed by recrystallisation from ethyl acetate/petroleum ether gave a sample of 1-(2-methoxyphenyl)-4-oxo-6-methoxy2,3,4,5-tetrahydropyrrolo[3,2-c]quinoline (0.6 g), m.p. 204°–205°.

$C_{19}H_{18}N_2O_3$. 0.03EtOAc: Found: C 70.44, H 5.48, N 8.49. Requires: C 70.66, H 5.66, N 8.62.

The bulk of the material was recrystallised once from ethyl acetate/petroleum ether, then used in subsequent synthetic steps without further purification.

EXAMPLE 10

Preparation of 1-(2-methoxyphenyl)-4-chloro-6-methoxy-2,3-dihydropyrrolo[3,2-c]quinoline 1-(2-Methoxyphenyl)-4-oxo-6-methoxy-2,3,4,5-tetrahydropyrrolo[3,2-c]quinoline (9.55 g) was dissolved in phosphoryl chloride (100 ml) and heated at reflux for 2.5 hours. After cooling, the solution was poured onto ice, made alkaline with aqueous sodium hydroxide solution, and extracted with dichloromethane. The organic extract was dried and evaporated, and the crude product purified by chromatography (silica gel, 50–100% diethyl ether in petroleum ether). The first compound to elute was 4-chloro-6-methoxy-2,3-dihydrofuro[3,2-c]quinoline, m.p. 99°–101°. Later fractions containing the desired product were recrystallised from ethyl acetate, then ethyl acetate/ethanol to give 1-(2-methoxyphenyl)-4-chloro-6-methoxy-2,3-dihydropyrrolo[3,2-c]quinoline, m.p. 183°–184°.

$C_{19}H_{17}ClN_2O_2$: Found: C 67.03, H 5.02, N 8.15, Cl 10.66. Requires: C 66.96, H 5.03, N 8.22, Cl 10.40.

EXAMPLE 11

Preparation of 1-(2-methoxyphenyl)-6-methoxy-2,3-dihydropyrrolo[3,2-c]quinoline hydrochloride A suspension of 1-(2-methoxyphenyl)-4-chloro-6-methoxy-2,3-dihydropyrrolo[3,2-c]quinoline (2.5 g, 7.3 mmol) in ethanol (250 ml) was hydrogenated over 10% palladium on charcoal at an initial pressure of 4 bar.

After 2.25 hours the solution was filtered through celite and evaporated. Crystallisation from ethanol/ethyl acetate gave 1-(2-methoxyphenyl)-6-methoxy-2,3-dihydropyrrolo[3,2-c]quinoline hydrochloride as a hygroscopic solid (1.05 g, 42%), m.p. 213°–214° (dec).

$C_{19}H_{18}N_2O_2$. HCl. 0.3$H_2O$. Found: C 65.49, H 5.41, N 7.99. Requires: C 65.53, H 5.67, N 8.04.

The mother liquors from the crystallisation were converted to the free base to give an oil which slowly crystallised (1.15 g, 51%), m.p. 173°–176°.

EXAMPLE 12

Preparation of 1-(2-methoxyphenyl)-4-amino-6-methoxy-2,3-dihydropyrrolo[3,2-c]quinoline 1-(2-Methoxyphenyl)-4-oxo-6-methoxy-2,3,4,5-tetrahydropyrrolo[3,2-c]quinoline (1.5 g) and phenyl phosphorodiamidate (2.5 g) were fused at 230° C. After 45 minutes the mixture was diluted with diphenyl ether (10 ml), further phenyl phosphorodiamidate (2 g) added, and heated for a further 15 minutes at 230° C. Aqueous sodium hydroxide was added and the product extracted into dichloromethane. Chromatography (silica gel. 2.5–4% methanolic ammonia in dichloromethane) to remove unchanged starting material was followed by recrystallisation from ethanol/ethyl acetate to yield 1-(2-methoxyphenyl)-4-amino-6-methoxy-2,3-dihydropyrrolo[3,2-c]quinoline (0.36 g), m.p. 244°–247° (dec).

$C_{19}H_{19}N_3O_2$. 0.03EtOH. 0.02EtOAc: Found: C 70.69, H 5.86, N 12.79. Requires: C 70.85, H 6.00, N 12.95.

EXAMPLE 13

Preparation of 1-(2-methylphenyl)-4-dimethylamino-6-methyl-2,3-dihydropyrrolo[3,2-c]quinoline A. Preparation of 2-(2-ethoxyethyl)-N,N'-di(2-methylphenyl)malonodiamide A mixture of o-methylaniline (74 ml, 0.68 mol) and diethyl 2-ethoxyethylmalonate (80 g, 0.34 mol) was heated to 220° C. as nitrogen was bubbled slowly through the mixture, and ethanol allowed to distill off. After 2.5 hours the crude product was allowed to cool, and triturated with petroleum ether. The solid was filtered off and washed with petroleum ether to give 2-(2-ethoxyethyl)-N,N'-di(2-methylphenyl)malonodiamide (270 g), which was used without further purification.

B. Preparation of 1-(2-methylphenyl)-4-oxo-6-methyl-2,3,4,5-tetrahydropyrrolo[3,2-c]quinoline 2-(2-Ethoxyethyl)-N,N'-di(2-methylphenyl)-malonodiamide (90 g) was stirred for 15 hours in diphenyl ether (250 ml) at reflux, then the diphenyl ether evaporated off in vacuo. Crystallisation of the residue from petroleum ether gave 1-(2-methylphenyl)-4-oxo-6-methyl-2,3,4,5-tetrahydropyrrolo[3,2-c]quinoline (21 g), which was used without further purification.

C. Preparation of 1-(2-methylphenyl)-4-chloro-6-methyl-2,3-dihydropyrrolo[3,2-c]quinoline 1-(2-Methylphenyl)-4-oxo-6-methyl-2,3,4,5-tetrahydropyrrolo[3,2-c]quinoline (16 g) was dissolved in phosphoryl chloride (100 ml) and heated at reflux for 5 hours. After cooling, the solution was poured onto ice, made alkaline with aqueous sodium hydroxide solution, and extracted with dichloromethane, which was dried and evaporated. Crystallisation from ethyl acetate gave 1-(2-methylphenyl)-4-chloro-6-methyl-2,3-dihydropyrrolo-[3,2-c]quinoline, which was used without further purification.

D. Preparation of 1-(2-methylphenyl)-4-dimethylamino-6-methyl-2,3-dihydropyrrolo[3,2-c]quinoline 1-(2-Methylphenyl)-4-chloro-6-methyl-2,3-dihydropyrrolo[3,2-c]quinoline (1.5 g. 4.9 mmol) and dimethylamine (33% in ethanol. 150 ml) were heated to 180° C. in a pressure vessel for 18 hours, then evaporated, taken up in dichloromethane, washed with sodium bicarbonate, dried and evaporated. Crystallisation from aqueous ethanol gave 1-(2-methylphenyl)-4-dimethylamino- 6-methyl-2,3-dihydropyrrolo[3,2-c]quinoline (0.97 g, 63%), m.p. 120°–121°.

$C_{21}H_{23}N_3$. $0.1H_2O$: Found: C 79.06, H 7 31, N 13,20. Requires: C 79.01, H 7.33, N 13.16.

EXAMPLE 14

Preparation of 1-(2-methylphenyl)-4-methylamino-6-methyl-2,3-dihydropyrrolo[3,2-c]quinoline 1-(2-Methylphenyl)-4-chloro-6-methyl-2,3-dihydropyrrolo[3,2-c]quinoline (1.5 g. 4.9 mmol) and methylamine (33% in ethanol, 250 ml) were heated to 180° C. in a pressure vessel for 24 hours, then evaporated. Crystallisation from aqueous ethanol gave 1-(2-methylphenyl)-4-methylamino-6-methyl-2,3-dihydropyrrolo[3,2-c]quinoline (1.05 g, 71%). m.p. 165°–167°.

$C_{20}H_{21}N_3$. $0.1H_2O$: Found: C 78.77, H 6.89, N 13.78. Requires: C 78.71, H 7.00, N 13.77.

EXAMPLE 15

Preparation of 1-(2-methylphenyl)-4-amino-6-methyl-2,3-dihydropyrrolo[3,2-c]quinoline Impure 1-(2-methylphenyl)-4-oxo-6-methyl-2,3,4,5-tetrahydropyrrolo[3,2-c]quinoline (10.0 g) and phenyl phosphorodiamidate (12 g) were fused at 230° C. After 30 minutes the mixture was diluted with diphenyl ether (50 ml), further phenyl phosphorodiamidate (4 g) added, and heated for a further 30 minutes at 230° C. Aqueous sodium hydroxide was added and the product extracted into dichloromethane. Chromatography (silica gel, 3% methanolic ammonia in dichloromethane) to remove unchanged starting material was followed by recrystallisation from ethanol to yield 1-(2-methylphenyl)-4-amino-6-methyl-2,3-dihydropyrrolo[3,2-c]quinoline (1.51 g), m.p. 173°–174°.

$C_{19}H_{19}N_3$: Found: C 78.80, H 6.70, N 14.55. Requires: C 78.86, H 6 62, N 14.52.

EXAMPLE 16

Preparation of 1-(2-methylphenyl)-6-methyl-2,3-dihydropyrrolo[3,2-c]quinoline 1-(2-Methylphenyl)-4-chloro-6-methyl-2,3-dihydropyrrolo[3,2-c]quinoline (1.5 g) in ethanol (100 ml) was hydrogenated over 10% palladium on charcoal (0 25 g) at an initial pressure of 3 bar. After 7 hours the mixture was filtered through celite and evaporated. Conversion to free base and recrystallisation from ethyl acetate/petroleum ether yielded 1-(2-methylphenyl)-6-methyl-2,3-dihydropyrrolo[3,2-c]quinoline (0.11 g, 31 %), m.p. 109°–110°.

$C_{19}H_{18}N_2$: Found: C 83.05, H 6.69, N 10.20. Requires: C 83.18, H 6.61, N 10.21.

EXAMPLE 17

Preparation of 1-(2-methylphenyl)-4-methoxy-6-methyl-2,3-dihydropyrrolo[3,2-c]quinoline 1-(2-Methylphenyl)-4-chloro-6-methyl-2,3-dihydropyrrolo[3,2-c]quinoline (0.62 g, 2 mmol), sodium methoxide (1.0 g, 18.5 mmol) and methanol (30 ml) were heated to 170° C. in a pressure vessel for 18 hours, then the solvent evaporated in vacuo. Conversion to free base, chromatography (silica gel. 40:60 dichloromethane/petroleum ether) and recrystallisation from methanol yielded 1-(2-methylphenyl)-4-methoxy-6-methyl-2,3-dihydropyrrolo- [3,2-c]quinoline (0.30 g), m.p. 107°–108°.

$C_{20}H_{20}N_2O$: Found: C 78.88, H 6.63, N 9.15. Requires: C 78.92, H 6.62, N 9.20.

EXAMPLE 18

Preparation of 1-(2-methylphenyl)-4-(3-hydroxypropylamino)-6-methylpyrrolo[3,2-c]quinoline A. Preparation of 1-(2-methylphenyl)-4-oxo-6-methyl-4,5-dihydropyrrolo[3,2-c]quinoline 1-(2-Methylphenyl)-4-oxo-6-methyl-2,3,4,5-tetrahydropyrrolo[3,2-c]quinoline (9.25 g), diphenyl ether (75 ml) and 10% palladium on charcoal (1 g) were heated at reflux for 4 hours, cooled, diluted with ethyl acetate, and filtered through celite. Further dilution with ethyl acetate induced crystallisation of 1-(2-methylphenyl)-4-oxo-6-methyl-4,5-dihydropyrrolo[3,2-c]quinoline (6.68 g), m.p. 226°–232°, which was used without further purification.

B. Preparation of 1-(2-methylphenyl)-4-chloro-6-methylpyrrolo[3,2-c]quinoline 1-(2-Methylphenyl)-4-oxo-6-methyl-4,5-dihydropyrrolo[3,2-c]quinoline (4.75 g) and phosphoryl chloride (40 ml) were heated at reflux for 1.5 hours. The phosphoryl chloride was evaporated in vacuo, the residue poured onto ice and extracted with dichloromethane, which was dried and evaporated. Crystallisation from ethanol yielded 1-(2-methylphenyl)-4-chloro-6-methylpyrrolo[3,2-c]quinoline (4.76 g), m.p. 135°–137°.

C. Preparation of 1-(2-methylphenyl)-4-(3-hydroxypropylamino)-6-methylpyrrolo[3,2-c]quinoline 1-(2-Methylphenyl)-4-chloro-6-methylpyrrolo[3,2-c]quinoline (1.0 g) and 3-aminopropanol (3.0 g) were heated to 150° C. for 3 hours. Chromatography (silica gel, 2% methanolic ammonia in dichloromethane) and recrystallisation from ethyl acetate/petroleum ether yielded 1-(2-methylphenyl)-4-(3-hydroxypropylamino)-6-methylpyrrolo[3,2-c]quinoline (0.57 g), m.p. 135°–137°.

$C_{22}H_{23}N_3O$. 0.02EtOAc: Found: C 76.16, H 6.75, N 12.15. Requires: C 76.38, H 6.72, N 12.10.

EXAMPLE 19

Preparation of 1-(2-methylphenyl)-4-(2-hydroxyethylamino)-6-methylpyrrolo[3,2-c]quinoline 1-(2-Methylphenyl)-4-chloro-6-methylpyrrolo[3,2-c]quinoline (1.0 g) and ethanolamine (3.0 g) were heated to 150° C. for 3 hours. Chromatography (silica gel, 2% methanolic ammonia in dichloromethane) and recrystallisation from ethyl acetate/petroleum ether yielded 1-(2-methylphenyl)-4-(2-hydroxyethylamino)-6methylpyrrolo[3,2-c]quinoline (0.78 g), m.p. 187°–188°.

$C_{21}H_{21}N_3O$: Found: C 76.57, H 6.28, N 12.83. Requires: C 76.11, H 6.39, N 12.68.

EXAMPLE 20

Preparation of 1-(2-methylphenyl)-4-methylamino-6-methylpyrrolo[3,2-c]quinoline 1-(2-Methylphenyl)-4-chloro-6-methylpyrrolo[3,2-c]quinoline (1.5 g, 4.9 mmol) and methylamine (33% in ethanol, 50 ml) were heated to 150° C. in a pressure vessel for 16 hours, then the solvent evaporated. Chromatography (silica gel, 2% methanolic ammonia in dichloromethane) and recrystallisation from aqueous ethanol yielded 1-(2-methylphenyl)-4-methylamino-6-methylpyrrolo[3,2-c]quinoline (0.62 g), m.p. 129°–130°.

$C_{20}H_{19}N_3$: Found: C 79.80, H 6.47, N 13.94. Requires: C 79.70, H 6.35, N 13.94.

EXAMPLE 21

Preparation of 2-(methylphenyl)-4-methyl-6-fluoro-2,3-dihydropyrrolo [3,2-c]quinoline A. Preparation of 3-(2-chloroethyl)-4-chloro-8-fluoro-2-methylquinoline 2-Fluoroaniline (9,65 ml, 0.1 mol) and 2-acetylbutyrolactone (10.76 ml, 0.1 mol) were heated to 120° for 1 hour, then 160° for 2 hours. The mixture was cooled, phosphoryl chloride (100 ml) added, and the resulting solution heated at reflux for 1.5 hours. After cooling, the mixture was poured onto ice and extracted with dichloromethane, which was washed with sodium bicarbonate solution, water and brine, dried and evaporated. Trituration with ether followed by recrystallisation from ethanol gave 3-(2-chloroethyl)-4-chloro-8-fluoro-2-methylquinoline (3.68 g), m.p. 101°–103°.

B. Preparation of 2-(methylphenyl)-4-methyl-6-fluoro-2,3-dihydropyrrolo[3,2-c]quinoline 3-(2—Chloroethyl)-4-chloro-8-fluoro-2-methylquinoline (2.58 g, 10 mmol) and 2-methylaniline hydrochloride (2.87 g, 20 mmol) in 2-propanol (25 ml) were heated to 170° in a pressure vessel for 18 hours. The solvent was evaporated, the residue taken up in dichloromethane and washed with sodium bicarbonate solution. Evaporation of the dichloromethane, trituration with ether, and recrystallisation from methanol then ethyl acetate gave 2-(methylphenyl)-4-methyl-6-fluoro-2,3-dihydropyrrolo[3,2c]quinoline (0.85 g), m.p. 209°–211°.

$C_{19}H_{17}FN_2$: Found: C 78.24, H 5.87, N 9 59. Requires: C 78.06, H 5.86, N 9.58.

EXAMPLE 22

Preparation of 1-(2-methylphenyl)-4-methylthio-6-methyl-2,3-dihydropyrrolo[3,2-c]quinoline 1-(2-Methylphenyl)-4-chloro-6-methyl-2,3-dihydro pyrrolo-[3,2-c]quinoline (1.54 g, 5 mmol) and sodium methanethiolate (1.40 g, 20 mmol) in 2-propanol (25 ml) were heated at 170° in a pressure vessel for 18 hours. The solvent was evaporated, the residue taken up in dichloromethane and washed with sodium bicarbonate solution. Chromatography (silica gel, dichloromethane) and crystallisation from methanol gave 1-(2-methylphenyl)-4-methylthio-6-methyl-2,3-dihydropyrrolo-[3,2-c]quinoline (0.8 g), m.p. 111°–113°.

$C_{20}H_{20}N_2S$. 0.2MeOH: Found: C 74.26, H 6.15, N 8.59, S 9.93. Requires: C 74.23, H 6.41, N 8.57, S 9.81.

EXAMPLE 23

Preparation of 1-(2-methylphenyl)-4-hydroxymethyl-2,3-dihydropyrrolo[3,2-c]quinoline A. Preparation of 1-(2-methylphenyl)-4-methyl-5-oxo-2,3-dihydropyrrolo[3,2-c]quinoline 1-(2-Methylphenyl)-4-methyl-2,3-dihydropyrrolo[3,2-c]quinoline (15.0 g, 0.055 mol) was stirred at 0° C. in chloroform (200 ml). A solution of m-chloroperoxybenzoic acid (9.5 g, 0.055 mol) in chloroform (100 ml) was added dropwise keeping the temperature below 5° C. The mixture was stirred for a further 30 minutes and the solvent then evaporated. The residue gas chromatographed (silica gel, 2% methanolic ammonia in dichloromethane) to afford 1-(2-methylphenyl)-4-methyl-5-oxo-2,3-dihydropyrrolo[3,2-c]quinoline (1.8 g, 11.3%) m.p. 212°–4°.

B. Preparation of 1-(2-methylphenyl)-4-hydroxymethyl-2,3-dihydropyrrolo[3,2-c]quinoline 1-(2-Methylphenyl)-4-methyl-5-oxo-2,3-dihydropyrrolo[3,2-c]quinoline (3.5 g, 0.0155 mol) was heated in acetic anhydride (75 ml) over a steam bath for 30 minutes. The solvent was evaporated and the residue was again heated over a steam bath in 10% hydrochloric acid for 45 minutes, when cool the solution was neutralised with sodium bicarbonate and extracted into dichloromethane. The organic solution was dried and evaporated then chromatographed (silica gel, 2% methanolic ammonia in dichloromethane) to afford 1-(2-methylphenyl)-4-hydroxymethyl-2,3-dihydropyrrolo[3,2-c]quinoline as crystals from ethyl acetate (0.56 g. 16%) m.p. 164°–6°.

$C_{19}H_{18}N_2O$: Requires: C 78.59, H 6.25, N 9.65. Found: C 78.32, H 6.25, N 9.58.

EXAMPLE 24

Preparation of 1-(2-methylphenyl)-5-oxo-7-methoxy-1,2,3,4,5,6-hexahydropyridino[3,2-c]quinoline A. Preparation of 1-(2-methylphenyl)-7-methoxy-6-oxo-1,2,3,4-tetrahydropyridino[3,2-c]quinoline 1-(2-methylphenyl)-7-methoxy-1,2,3,4-tetrahydropyridino-[3,2-c]quinoline (0.26 g, 0.85 mmol) was stirred at 0°–5° C. in chloroform (20 ml) and m-chloroperoxybenzoic acid (0.15 g) in chloroform (2 ml) was added. Stirring was continued at 0° C. for 2 hours.

The solvent was evaporated and the residue was chromatographed (silica gel, 2-3% methanolic ammonia in dichloromethane) to afford the required 1-(2-methylphenyl)-7-methoxy-6-oxo-1,2,3,4-tetrahydropyridino[3,2-c]quinoline (0.08 g, 29%).

B. Preparation of 1-(2-methylphenyl)-5-oxo-7-methoxy-1,2,3,4,5,6-hexahydropyridino[3,2-c]quinoline 1-(2-methylphenyl)-7-methoxy-6-oxo-1,2,3,4-tetrahydropyridino-[3,2-c]quinoline (0.08 g, 0.25 mmol) was heated over a steam bath in acetic anhydride (10 ml) for 40 minutes. The solvent was evaporated and the residue was reheated over a steam bath in 10% hydrochloric acid (10 ml) for 30 minutes. The product was extracted into chloroform and chromatographed (silica gel. 1% methanol in chloroform) to give 1-(2-methylphenyl)-5-oxo-7-methoxy-1,2,3,4,5,6-hexahydropyridino[3,2-c]-quinoline (5 mg) m.p. 203°-5°.

EXAMPLE 25

Preparation of 1-(2-methylphenyl)-4-(4-hydroxybutylamino)-6-methylpyrrolo[3,2-c]quinoline hydrochloride 1-(2-methylphenyl)4-chloro-6-methylpyrrolo[3,2-c]quinoline (1.0 g, 3,26 mmol) was dissolved in 4-aminobutanol (3.0 g) and stirred for 6 hours at 170°. Chromatography (silica gel, 2% methanolic ammonia in dichloromethane), conversion to the hydrochloride and recrystallisation from ethanol/ether gave 1-(2-methylphenyl)-4-(4-hydroxybutylamino)-6-methylpyrrolo[3,2-c]quinoline hydrochloride (0.8 g), m.p. 176°-178°.

$C_{23}H_{25}N_3O.HCl.0.2H_2O$: Found: C 69.31, H 6.67, N 10.53, Cl 8.59. Requires: C 69.30, H 6.65, N 10.54, Cl 8.89.

EXAMPLE 26

Preparation of 1-(4-hydroxy-2-methylphenyl)-4-methyl-2,3-dihydropyrrolo[3,2-c]quinoline A solution of 4-chloro-3-chloroethyl-2-methylquinoline hydrochloride (1.28 g, 4,6 mmol) and 4-hydroxy-2-methylaniline (1.13 g. 9.2 mmol) in n-butanol (20 ml) was heated at reflux under a nitrogen atmosphere for 20 hours, then evaporated. Chromatography (silica gel, 5-7% methanolic ammonia in dichloromethane) and recrystallisation from aqueous methanol gave 1-(4-hydroxy2-methylphenyl)-4-methyl-2,3-dihydropyrrolo[3,2-c]quinoline (0.16 g), m.p. 315°-318°.

$C_{19}H_{18}N_2O$: Found: C 78.55, H 6.27, N 9.56. Requires: C 78.59, H 6.25, N 9.65.

EXAMPLE 27

Preparation of 1-(4-methoxy-2-methylphenyl)-4-methyl-6-methoxy-2,3-dihydropyrrolo[3,2-c]quinoline A mixture of 2-methyl-3-(2-chloroethyl)-4-chloro-8-methoxyquinoline hydrochloride (15.33 g, 50 mmol), 4-methoxy-2-methylaniline (9.0 ml. 70 mmol) and 2-propanol (200 ml) was heated at reflux for 2 days, then evaporated. The crude product was triturated with ether then recrystallised twice from aqueous ethanol to give the title compound (3.16 g), m.p. 163°-167°.

$C_{21}H_{22}N_2O_2$. $0.9H_2O$: Found: C 72.02, H 6.84, N 7.98. Requires: C 71.93, H 6.84, N 7.99.

EXAMPLE 28

Preparation of 1-(2.6-dimethylphenyl)-4-methyl-2,3-dihydropyrrolo[3,2-c]quinoline A mixture of 2-methyl-3-(2-chloroethyl)-4-chloroquinoline hydrochloride (13.8 g, 50 mmol), 2,6-dimethylaniline (12.5 ml, 100 mmol) and 2-propanol (400 ml) was heated to 140° for 5 days in a pressure vessel, then cooled and evaporated. The crude product was converted to free base and chromatographed (silica gel, methanolic ammonia in dichloromethane). Recrystallisation from aqueous methanol followed by aqueous ethanol gave 1-(2,6-dimethylphenyl)-4-methyl- 2,3-dihydropyrrolo[3,2-c]quinoline (1.52 g), m.p. 149°-152°.

$C_{20}H_{20}N_2$: Found: C 83.02, H 6.99, N 9.65. Requires: C 83.30, H 6.99, N 9.71.

EXAMPLE A

A tablet for oral administration is prepared by combining

|  | Mg/Tablet |
| --- | --- |
| Compound of structure (I) | 100 |
| Mannitol | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration was prepared from the following

| Compound of Structure 1 | 6.68% (w:v) |
| --- | --- |
| 1M citric acid | 30% (v:v) |
| sodium hydroxide (qs) | to pH 3.2 |
| water for injection EP | to 100 ml |

The compound of Structure 1 was dissolved in the citric acid and the pH slowly adjusted to pH 3,2 with the sodium hydroxide solution. The solution was then made up to 100 ml with water, sterilized by filtration and sealed into appropriately sized ampoules and vials.

Biological Data (A) $H^+K^+$ ATPase Activity

The effects of a single high concentration (100 μM) of a compound of structure (I) on K-stimulated ATPase activity in lyophilised gastric vesicles was determined. Preferred compounds of structure (1) were also tested over a range of concentrations to determine $IC_{50}$ values.

(i) Preparation of lyophilised gastric vesicles (H/K-ATpase)

Lyophilised gastric vesicles were prepared from pig fundic mucosa after the method of Keeling et, al. (Biochem. Pharmacol., 34, 2967, 1985).

(ii) $K^+$-stimulated ATpase activity $K^+$-stimulated ATpase activity was determined at 37° C. in the presence of the following: 10 mM pipes/-

Tris buffer pH 7.0, 2 mM MgSO$_4$, 1 mM KCl, 2 mM Na$_2$ATp and 3 μg protein/ml lyophilised gastric vesicles. After incubation for 30 minutes, the inorganic phosphate hydrolysed from ATp was determined by the method of Yoda and Hokin (Biochem. Biophys. Res. Commun. 40, 880, 1970).

Compounds of structure (I) were dissolved in dimethylsulphoxide which up to the highest concentration used had no effect on K$^+$-stimulated ATpase activity.

The effect of the highest concentration of each compound of structure (I) on the recovery of a standard amount of inorganic phosphate was also determined.

(iii) Results

The compounds of each of examples 1 to 16 and 18 to 21, 23 and 25 to 28 were assayed in the above-noted screen and found to have IC$_{50}$ values in the range of from 0.17 to 33 μM.

What is claimed is:

1. A compound of structure (I)

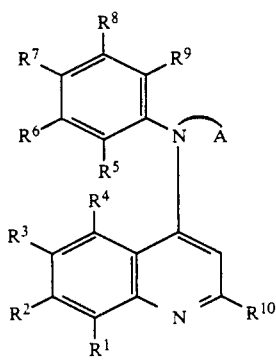

(I)

in which
R$^1$ to R$^4$ are the same or different and are each hydrogen, C$_{1-4}$alkyl, C$_{1-6}$alkoxy, phenyl, C$_{1-6}$alkylthio, C$_{1-4}$alkanoyl, amino, C$_{1-6}$alkylamino, diC$_{1-6}$alkylamino, halogen, trifluoromethyl or nitro, provided that at least two of R$^1$ to R$^4$ are hydrogen.
R$^5$ to R$^9$ are the same or different and are each hydrogen, C$_{1-6}$alkyl, C$_{1-6}$alkoxy, C$_{1-6}$alkylthio, halogen, cyano, amino, hydroxy, carbamoyl, carboxy, C$_{1-6}$alkanoyl, trifluoromethyl or nitro, provided that at least two of R$^5$ to R$^9$ are hydrogen;
R$^{10}$ is hydrogen, C$_{1-6}$alkyl, C$_{1-6}$alkoxy, halogen, hydroxy, —CH$_2$OH, C$_{1-6}$alkylthio, NH(CH$_2$)$_n$OH in which n is 0 to 4 or a group —NR$^{11}$R$^{12}$ in which R$^{11}$ and R$^{12}$ are the same or different and are each hydrogen or C$_{1-6}$alkyl; and
A is —(CH$_2$)$_2$—, —(CH$_2$)$_3$— or —CH=CH—; provided that
(1) when R$^1$ to R$^6$ and R$^8$ and R$^9$ are each hydrogen, R$^7$ is hydroxy and R$^{10}$ is methyl, A is —(CH$_2$)$_3$— or —CH=CH—;
(2) when R$^1$ to R$^9$ are each hydrogen and R$^{10}$ is chlorine, A is —(CH$_2$)$_3$—;
(3) when R$^1$ to R$^{10}$ are each hydrogen, A is —(CH$_2$)$_3$—;
(4) when R$^1$ and R$^2$ and R$^4$ to R$^{10}$ are each hydrogen and R$^3$ is methoxy, A is —(CH$_2$)$_2$— or —(CH$_2$)$_3$—;
(5) when A is —(CH$_2$)$_2$—, and R$^5$ or R$^9$ is chloro, or when A is —(CH$_2$)$_2$—, and R$^7$ is methoxy or methyl, two of the following conditions are present;
(i) one other of R$^5$ to R$^9$ is other than H;
(ii) one of R$^2$ to R$^4$ is other than H;
(iii) R$^1$ is other than OH, OCH$_3$ or H; or
(iv) R$^{10}$ is other than methyl;
(6) when A is —(CH$_2$)$_2$— and one of R$^5$, R$^6$, R$^8$ or R$^9$ is methyl or methoxy, or when A is —(CH$_2$)$_2$— and R$^6$, R$^7$ or R$^8$ are chloro, one of the following conditions is present;
(i) one other of R$^5$ to R$^9$ are other than H;
(ii) one of R$^2$ to R$^4$ is other than H;
(iii) R$^1$ is other than OH, OCH$_3$ or H; or
(iv) R$^{10}$ is other than methyl;
(7) when A is —(CH$_2$)$_2$— and one of R$^7$ is ethyl or ethoxy, or when A is —(CH$_2$)$_2$— and R$^5$ or R$^9$ are fluoro or bromo, one of the following conditions is present;
(i) one other of R$^5$ to R$^9$ are other than H;
(ii) one of R$^2$ to R$^4$ is other than H;
(iii) R$^1$ is other than OH, OCH$_3$ or H;
(iv) R$^{10}$ is other than methyl;
or a pharmaceutically acceptable salt thereof.

2. A compound according to claim 1 in which A is —(CH$_2$)$_2$—.

3. A compound according to claim 1 in which A is —CH=CH—.

4. A compound according to any one of claims 1 to 3 in which R$^{10}$ is a group —NR$^{11}$R$^{12}$ in which R$^{11}$ and R$^{12}$ are as described for structure (I).

5. A compound according to any one of claims 1 to 3 in which R$^{10}$ is C$_{1-6}$alkyl.

6. A compound according to any one of claims 1 to 5 in which R$^1$ is C$_{1-6}$alkyl or C$_{1-6}$alkoxy.

7. A compound according to claim 6 in which R$^9$ is C$_{1-6}$alkyl.

8. A compound according to claim 1 which is 1-(2-methylphenyl)-4-methyl-6-methoxypyrrolo[3,2-c]quinoline.

9. A compound according to claim 1 which is 1-(2-methylphenyl)-4,6-dimethyl-2,3-dihydropyrrolo[3,2-c]quinoline.

10. A compound according to claim 1 which is 1-(2-methylphenyl)-7-methoxy-1,2,3,4-tetrahydropyridino[3,2-c]quinoline.

11. A compound according to claim 1 which is 1-(2-methoxyphenyl)-4-chloro-6-methoxy-2,3-dihydropyrrolo[3,2-c]quinoline.

12. A compound according to claim 1 which is 1-(2-methoxyphenyl)-6-methoxy-2,3-dihydropyrrolo[3,2-c]quinoline hydrochloride.

13. A compound according to claim 1 which is 1-(2-methoxyphenyl)-4-amino-6-methoxy-2,3-dihydropyrrolo[3,2-c]quinoline.

14. A compound according to claim 1 which is 1-(2-methylphenyl)-4-dimethylamino-6-methyl-2,3-dihydropyrrolo[3,2-c]quinoline.

15. A compound according to claim 1 which is 1-(2-methylphenyl)-4-methylamino-6-methyl-2,3-dihydropyrrolo[3,2-c]quinoline.

16. A compound according to claim 1 which is 1-(2-methylphenyl)-4-amino-6-methyl-2,3-dihydropyrrolo[3,2-c]quinoline.

17. A compound according to claim 1 which is 1-(2-methylphenyl)-6-methyl-2,3-dihydropyrrolo[3,2-c]quinoline.

18. A compound according to claim 1 which is 1-(2-methylphenyl)-4-methoxy-6-methyl-2,3-dihydropyrrolo[3,2-c]quinoline.

19. A compound according to claim 1 which is 1-(2-methylphenyl)-4-(3-hydroxypropylamino)-6-methyl-pyrrolo[3,2-c]quinoline.

20. A compound according to claim 1 which is 1-(2-methylphenyl)-4-(2-hydroxyethylamino)-6-methylpyrrolo[3,2-c]quinoline.

21. A compound according to claim 1 which is 1-(2-methylphenyl)-4-methylamino-6-methylpyrrolo[3,2-c]quinoline.

* * * * *